United States Patent
Koradin et al.

(10) Patent No.: US 7,754,749 B2
(45) Date of Patent: Jul. 13, 2010

(54) DERIVATIVES OF A 1-PHENYLTRIAZOLE

(75) Inventors: Christopher Koradin, Ludwigshafen (DE); Wolfgang Von Deyn, Neustadt (DE); Michael Rack, Eppelheim (DE); Thomas Zierke, Böhl-Iggelheim (DE); David G. Kuhn, Apex, NC (US); Deborah L. Culbertson, Fuquay-Varina, NC (US); Douglas D. Anspaugh, Apex, NC (US); Hassan Oloumi-Sadeghi, Raleigh, NC (US)

(73) Assignee: BASF Aktiengesellschaft, Ludwigshafen (DE)

( * ) Notice: Subject to any disclaimer, the term of this patent is extended or adjusted under 35 U.S.C. 154(b) by 439 days.

(21) Appl. No.: 11/915,938

(22) PCT Filed: May 30, 2006

(86) PCT No.: PCT/EP2006/062719

§ 371 (c)(1),
(2), (4) Date: Nov. 29, 2007

(87) PCT Pub. No.: WO2006/128867

PCT Pub. Date: Dec. 7, 2006

(65) Prior Publication Data

US 2008/0200528 A1      Aug. 21, 2008

Related U.S. Application Data

(60) Provisional application No. 60/687,027, filed on Jun. 3, 2005.

(51) Int. Cl.
*A01N 43/653*     (2006.01)
*A61K 31/4196*    (2006.01)
*A01P 7/04*       (2006.01)
*C07D 249/08*     (2006.01)

(52) U.S. Cl. ................... 514/383; 548/269.4

(58) Field of Classification Search ............ None
See application file for complete search history.

(56) References Cited

FOREIGN PATENT DOCUMENTS

| EP | 0 285 893 | 10/1988 |
|---|---|---|
| EP | 0 604 798 | 7/1994 |
| EP | 0 957 094 | 11/1999 |
| WO | WO 00/24720 | 5/2000 |

OTHER PUBLICATIONS

International Preliminary Report on Patentability, issued Dec. 6, 2007, in corresponding International Patent Application No. PCT/EP2006/062719, filed May 30, 2006.

*Primary Examiner*—Kamal A Saeed
(74) *Attorney, Agent, or Firm*—Brinks Hofer Gilson & Lione

(57) ABSTRACT

Compounds of formula (I)

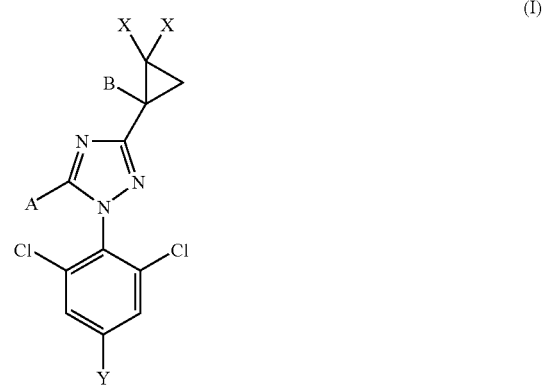

wherein
  X is chloro or bromo;
  Y is chloro or trifluoromethyl; and
  A and B are hydrogen or methyl with the proviso that one of A or B must be methyl; or the enantiomers or salts thereof,
use of compounds of formula I for combating insects or acarids and for treating, controlling, preventing or protecting animals against infestation or infection by parasites, and compositions comprising compounds of formula I.

13 Claims, No Drawings

DERIVATIVES OF A 1-PHENYLTRIAZOLE

This application is a National Stage application of International Application No. PCT/EP2006/062719, filed May 30, 2006, which claims the benefit of U.S. Provisional Application No. 60/687,027, filed Jun. 3, 2005, wherein the entire contents of both are hereby incorporated herein by reference.

The present invention relates to compounds of formula (I)

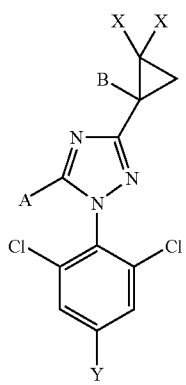

(I)

wherein

X is chloro or bromo;

Y is chloro or trifluoromethyl; and

A and B are hydrogen or methyl with the proviso that one of A or B must be methyl;

or the enantiomers or salts thereof for combating insects or acarids.

The present invention also provides methods for the control of insects and acarids by contacting the insect or acarid or their food supply, habitat or breeding grounds with a pesticidally effective amount of compounds or compositions of formula I.

Moreover, the present invention also relates to a method of protecting growing plants from attack or infestation by insects or acarids by applying to the foliage of the plants, or to the soil or water in which they are growing, with a pesticidally effective amount of compositions or compounds of formula I.

This invention also provides a method for treating, controlling, preventing or protecting animals against infestation or infection by parasites which comprises orally, topically or parenterally administering or applying to the animals a parasiticidally effective amount of compositions or compounds of formula I.

The invention also provides a process for the preparation of a composition for treating, controlling, preventing or protecting a warm-blooded animal or a fish against infestation or infection by insects and acarids which comprises a pesticidally effective amount of a compound having the formula I.

In spite of the commercial insecticides and acaricides available today, damage to crops, livestock, companion animals and humans still occurs. Accordingly, there is on-going research to create new and more effective insecticides and acaricides. It was therefore an object of the present invention to provide new insecticidal and acaricidal compounds, new compositions and new methods for the control of insects or acarids.

We have found that these objects are achieved by the compounds and compositions of formula I.

1-Phenyltriazoles have been described inter alia in EP-A 957 094 and in EP-A 285 893. The insecticidal and acaricidal properties of these compounds however are not totally satisfying.

It was therefore an object of the present invention to provide new 1-phenyltriazoles having enhanced properties for combating insects and acarids.

Accordingly, 1-phenyl-1,2,4-triazoles of formula I were found which exhibit a methyl group at the 1-position of the cyclopropyl ring and/or at the 5-position of the triazole ring.

EP-A 957 094 discloses 1-(2-halogenaryl)azoles wherein the aryl group may be substituted phenyl and the azole may be 1,2,4-triazole, which may carry an optionally substituted cyclopropyl ring. No mention is made however of the favorable effect of fixing a methyl group at the cyclopropyl ring or at the triazole ring.

EP-A 285 893 describes 1-phenyl-(1,2,4-triazoles) wherein the triazole in the 3-position among a broad group of substituents may carry a methyl-substituted cyclopropyl group but preferably an alkyl or haloalkyl group and in the 5-position is optionally substituted, preferably by an amino derived group. EP-A 285 893 does not disclose the 1-phenyltriazoles of the present invention nor does it suggest the favorable effect of fixing a methyl group at the cyclopropyl ring and/or at the triazole ring.

Depending on the substitution pattern, the compounds of formula I can contain a chiral center, in which case they are present as enantiomer mixtures. Subject-matter of this invention are not only compositions containing these mixtures but also those containing the pure enantiomers.

Compounds of formula I may be synthesized by reacting compounds of formula II

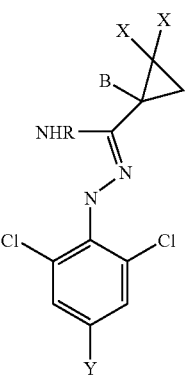

(II)

wherein R is methyl, ethyl or trimethylsilyl, with an oxidating agent.

Suitable oxidating agents are, for example, lead (IV)-oxide ($PbO_2$), hypochlorites (e.g. NaOCl) and dichlorodicyanobenzoquinone (DDQ).

Particular preference is given to dichlorodicyanobenzoquinone (DDQ).

The reaction is usually carried out at temperatures of from −20° C. to 50° C., preferably from −5° C. to 25° C. (room temperature), in an inert organic solvent in the presence of a base.

Suitable solvents are aromatic hydrocarbons such as toluene, o-, m- and p-xylene, aliphatic hydrocarbons such as pentane, hexane, cyclohexane and petroleum ether, halogenated hydrocarbons, such as methylene chloride, chloroform and chlorobenzene, ethers, such as diethyl ether, diisopropyl ether, tert.-butyl methyl ether, dioxane, tetrahydrofurane, diglyme or anisol, nitriles such as acetonitrile and propionitrile, and also dimethyl sulfoxide, dimethyl formamide and dimethyl acetamide. Particular preference is given to aromatic hydrocarbons. It is also possible to use mixtures of the solvents mentioned.

Suitable bases are organic bases, such as tertiary amines, such as trimethyl amine, triethyl amine, diisopropyl ethyl amine, N-methyl-piperidine, and pyridine. Substituted pyridines are for example collidine, lutidine and 4-dimethyl amino pyridine as well as bicyclic amines such as quinoline or isoquinoline. Further suitable bases are inorganic compounds such as alkali metal hydroxides and earth alkali metal hydroxides such as lithium hydroxide, sodium hydroxide, potassium hydroxide, and calcium hydroxide, alkali metal oxides and earth alkali metal oxides such as lithium oxide, sodium oxide, potassium oxide, calcium oxide, and magnesium oxide, alkali metal carbonates and earth alkali metal carbonates such as lithium carbonate, potassium carbonate, and calcium carbonate, alkali metal hydrogen carbonates such as sodium hydrogen carbonate, alkali metal alcoholates and earth alkali metal alcoholates such as sodium methanolate, sodium ethanolate, potassium ethanolate, potassium tert.-butanolate and dimethoxy magnesium. Particular preference is given to pyridine and substituted pyridines. It is also possible to use mixtures of the bases mentioned.

In general, the base is employed in equimolar amounts, in excess, or as a solvent.

Compounds of formula ll are obtainable according to procedures described in EP-A 604 798.

With respect to the intended use of the compounds of formula I, particular preference is given to the following meanings of the substituents, in each case on their own or in combination:

Preference is given to compounds of formula I wherein X is chloro.

Moreover, preference is given to compounds of formula I wherein Y is trifluoromethyl.

Preference is also given to compounds of formula I wherein A is methyl.

Moreover, preference is given to compounds of formula I wherein B is methyl.

Particular preference is given to compounds of formula I wherein A is methyl and X is chloro.

Particular preference is also given to compounds of formula I wherein B is methyl and X is chloro.

Particular preference is also given to compounds of formula I wherein A and B are each methyl.

Particularly preferred are the following compounds:

1) 1-(2,6-dichloro-4-trifluoromethylphenyl)-3-(1-methyl-2,2-dichlorocyclopropyl)-5-methyl-1,2,4-triazole; and 2) 1-(2,6-dichloro-4-trifluoromethylphenyl)-3-(2,2-dichlorocyclopropyl)-5-methyl-1,2,4-triazole.

The most preferred compound according to the present invention is 1-(2,6-dichloro-4-trifluoromethylphenyl)-3-(1-methyl-2,2-dichlorocyclopropyl)-5-methyl-1,2,4-triazole.

The compounds of the formula I are suitable for efficiently controlling insects and acarids in crop protection and in combating non-crop pests.

The compounds of the formula I are especially suitable for efficiently combating the following pests:

insects from the order of the lepidopterans (*Lepidoptera*), for example *Agrotis ypsilon, Agrotis segetum, Alabama argillacea, Anficarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalls, Dlatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Hellothis armigera, Hellothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalls, Panolls flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera fruglperda, Spodoptera littoralls, Spodoptera litura, Thaumatopoea pityocampa, Tortrix viridana, Trichoplusia ni* and *Zeiraphera canadensis*, beetles (Coleoptera), for example *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidals, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera* ssp., *Diabrotica longicornis, Diabrotica semipunctata, Diabrotica 12-punctata Diabrotica speciosa, Diabrotica virgifera, Epilachna varivestis, Epitrix hiirtpennis, Eutinobothrus brasiilensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllobius pyri, Phyllotreta chrysocephala, Phyllophaga* sp., *Phyllopertha horticola, Phyllotreta nemorum, Phyllotreta striolata, Popillia japonica, Sitona lineatus* and *Sitophilus granaria*, flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discails, Chrysops silacea, Chrysops allanticus, Cochliomyla hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Della radicum, Dermatobia hominis, Fannia canicularis, Geomyza Tripunctata, Gasterophilus intestinalis, Glossina morsiftans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilla sericata, Lycoria pectoralis, Mansonia titillanus, Mayetiola destructor, Musca domestica, Muscina stabulans, Oestrus ovis, Opomyza florum, Oscinella frit, Pegomya hysocyami, Phor-* bia antiqua, Phorbia brassicae, Phorbia coarctata, Phlebotomus argentipes, Psorophora columbiae, Psila rosae, Psorophora discolor, Prosimullum mixtum, Rhagoletis cerasi, Rhagoletis pomonella, Sarcophaga haemorrhoidalis, Sarcophaga sp., Simulium vittatum, Stomoxys calcitrans, Tabanus bovinus, Tabanus atratus, Tabanus lineola, and Tabanus similis, Tipula oleracea, and Tipulapaludosa thrips (Thysanoptera), e.g. Dichromothrips corbetti, Dichromothrips ssp, Frankliniella fusca, Frankllniella occidentalls, Frankllniella tritici, Scirtothrlps citri, Thrips olyzae, Thrips palmi and Thrips tabaci, termites (Isoptera), e.g. Calotermes flavicollis, Leucotermes flavipes, Heterotermes aureus, Reticulltermes flavipes, Retfculltermes virginicus, Reticulltermes lucifugus, Termes natalensis, and Coptotermes formosanus, cockroaches (Blattaria—Blattodea), e.g. Blattella germanica, Blattella asahinae, Periplaneta americana, Periplaneta japonica, Periplaneta brunnea, Periplaneta fuligginosa, Periplaneta australasiae, and Blatta orientalis, true bugs (Hemiptera), e.g. Acrosternum hilare, Blissus leucopterus, Cyrtopeltis notatus, Dysdercus cingulatus, Dysdercus intermedius, Eurygaster integriceps, Euschistus impictivenfris, Leptoglossus phyllopus, Lygus llneolaris, Lygus pratensis, Nezara viriduia, Piesma quadrata, Solubea insularis, Thyanta perditor, Acyrthosiphon onobrychis, Adelges laricis, Aphidula nasturti; Aphis fabae, Aphis forbesi, Aphis pomi, Aphis gossypii, Aphis grossulariae, Aphis schnideri, Aphis spiraecola, Aphis sambuci, Acyrthosiphon pisum, Aulacofthum solani, Bemisia argentifolii, Brachycaudus cardui, Brachycaudus helichrysi, Brachycaudus persicae, Brachycaudus prunicola, Brevicoryne brassicae, Capiftophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mall, Psylla piri, Rhopalomyzus ascalonicus, Rhopalosiphum maidis, Rhopalosiphum padi, Rhopalosiphum inserfum, Sappaphis mala, Sappaphis mali, Schizaphis graminum, Schizoneura lanuginosa, Sitobion avenae, Trialeurodes vaporariorum, Toxoptera aurantiiand, Viteus vitifolli, Cimex lectularius, Cimex hemipterus, Reduvius senilis, Triatoma spp., and Arilus critatus.

ants, bees, wasps, sawflies (Hymenoptera), e.g. Athalia rosae, Atta cephalotes, Atta capiguara, Atta cephalotes, Afta laevigata, Atta robusta, Atta sexdens, Atta texana, Crematogaster spp., Hoplocampa minuta, Hoplocampa testudinea, Monomorium pharaonls, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus spp. Vespula squamosa, Paravespula vulgaris, Paravespula pennsylvanica, Paravespula germanica, Dolichovespula maculata, Vespa crabro, Polistes rubiginosa, Camponotus floridanus, and Linepithema humile, crickets, grasshoppers, locusts (Orthoptera), e.g. Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americans, Schistocerca gregaria, Dociostaurus maroccanus, Tachycines asynamorus, Oedaleus senegalensis, Zonozerus variegatus, Hieroglyphus daganensis, Kraussaria angulifera, Calliptamus itallcus, Chortoicetes terminifera, and Locustana pardalina, Arachnoidea, such as arachnids (Acarina), e.g. of the families Argasidae, Ixodidae and Sarcoptidae, such as Amblyomma americanum, Amblyomma variegatum, Ambryomma maculatum, Argas persicus, Boophilus annulatus, Boophilus decoloratus, Boophilus microplus, Dermacentor silvarum, Dermacentor andersoni, Dermacentor variabllis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnini, Dermanyssus gallinae, Psoroptes ovis, Rhipicephalus sanguineus, Rhipicephalus appendiculatus, Rhipicephalus evertsi, Sarcoptes scabiei, and Eriophyidae spp. such as Aculus schlechtendali, Phyllocoptrata oleivora and Eriophyes sheldoni, Tarsonemidae spp. such as Phytonemus pallidus and Polyphagotarsonemus latus; Tenuipalpidae spp. such as Brevipalpus phoenicis; Tetranychidae spp. such as Tetranychus cinnabarinus, Tetranychus kanzawai, Tetranychus pacificus, Tetranychus telarius and Tetranychus urticae, Panonychus ulmi, Panonychus citri, and Oligonychus pratensis; Araneida, e.g. Lafrodectus mactans, and Loxosceles reclusa, fleas (Siphonaptera), e.g. Ctenocephalides felis, Ctenocephalides canis, Xenopsylla cheopis, Pulex irriftans, Tunga penefrans, and Nosopsyllus fasciatus, silverfish, firebrat (Thysanura), e.g. Lepisma saccharins and Thermobia domestics, centipedes (Chilopoda), e.g. Scutigera coleoptrata, millipedes (Diplopoda), e.g. Narceus spp., Earwigs (Dermaptera), e.g. forifcula auricularia, lice (Phthiraptera), e.g. Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus and Solenopotes capillatus.

Moreover, the compounds of formula I and compositions containing them are especially useful for the control of Isoptera, Diptera, Blattaria (Blattodea), Hymenoptera, Siphonaptera, and Acarina.

For use according to the present invention, the compounds I can be converted into the customary formulations, e.g. solutions, emulsions, suspensions, dusts, powders, pastes and granules. The use form depends on the particular purpose; it is intended to ensure in each case a fine and uniform distribution of the compound according to the invention.

The formulations are prepared in a known manner, e.g. by extending the active ingredient with solvents and/or carriers, if desired using emulsifiers and dispersants. Solvents/auxiliaries, which are suitable, are essentially:

water, aromatic solvents (for example Solvesso products, xylene), paraffins (for example mineral fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used.

carriers such as ground natural minerals (e.g. kaolins, clays, talc, chalk) and ground synthetic minerals (e.g. highly disperse silica, silicates); emulsifiers such as nonionic and anionic emulsifiers (e.g. polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol ®octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose and ethylene oxide/propylene oxide block copolymers.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dusts can be prepared by mixing or concomitantly grinding the active substances with a solid carrier.

Granules, for example coated granules, impregnated granules and homogeneous granules, can be prepared by binding the active ingredients to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

The following are examples of formulations:

1. Products for Dilution with Water

A Soluble concentrates (SL, LS)

10 parts by weight of a compound according to the invention are dissolved in water or in a water-soluble solvent. As an alternative, wetters or other auxiliaries are added. The active ingredient dissolves upon dilution with water.

B Dispersible concentrates (DC)

20 parts by weight of a compound according to the invention are dissolved in cyclohexanone with addition of a dispersant, for example polyvinylpyrrolidone. Dilution with water gives a dispersion.

C Emulsifiable concentrates (EC)

15 parts by weight of a compound according to the invention are dissolved in xylene with addition of calcium dodecylbenzenesulfonate and castor oil ethoxylate (in each case 5% strength). Dilution with water gives an emulsion.

D Emulsions (EW, EO, ES)

40 parts by weight of a compound according to the invention are dissolved in xylene with addition of calcium dodecylbenzenesulfonate and castor oil ethoxylate (in each case 5% strength). This mixture is introduced into water by means of an emulsifier (Ultraturrax) and made into a homogeneous emulsion. Dilution with water gives an emulsion.

E Suspensions (SC, OD, FS)

In an agitated ball mill, 20 parts by weight of a compound according to the invention are milled with addition of dispersant, wetters and water or an organic solvent to give a fine active ingredient suspension. Dilution with water gives a stable suspension of the active ingredient.

F Water-dispersible granules and water-soluble granules (WG, SG)

50 parts by weight of a compound according to the invention are ground finely with addition of dispersants and wetters and made into water-dispersible or water-soluble granules by means of technical appliances (for example extrusion, spray tower, fluidized bed). Dilution with water gives a stable dispersion or solution of the active ingredient.

G Water-dispersible powders and water-soluble powders (WP, SP, WS)

75 parts by weight of a compound according to the invention are ground in a rotor-stator mill with addition of dispersant, wetters and silica gel. Dilution with water gives a stable dispersion or solution with the active ingredient.

2. Products to be Applied Undiluted

H Dustable powders (DP, DS)

5 parts by weight of a compound according to the invention are ground finely and mixed intimately with 95% of finely divided kaolin. This gives a dustable product.

I Granules (GR, FG, GG, MG)

0.5 parts by weight of a compound according to the invention is ground finely and associated with 95.5% carriers. Current methods are extrusion, spray drying or the fluidized bed. This gives granules to be applied undiluted.

J ULV solutions (UL)

10 parts by weight of a compound according to the invention are dissolved in an organic solvent, for example xylene. This gives a product to be applied undiluted.

The active ingredients can be used as such, in the form of their formulations or the use forms prepared therefrom, eg. in the form of directly sprayable solutions, powders, gels, suspensions or dispersions, emulsions, oil dispersions, pastes, dustable products, materials for spreading, or granules, microcapsules (CS), pellets or tablets, by means of spraying, atomizing, dusting, spreading or pouring. The use forms depend entirely on the intended purposes; it is intended to ensure in each case the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within relatively wide ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even to apply the active ingredient without additives.

Various types of oils, wetters, adjuvants, herbicides, fungicides, other pesticides, or bactericides may be added to the active ingredients, if appropriate just immediately prior to use (tank mix). These agents usually are admixed with the agents according to the invention in a weight ratio of 1:10 to 10:1.

The compounds of formula I are effective through both contact (via soil, glass, wall, bed net, carpet, plant parts or animal parts), and ingestion (bait, or plant part) and through trophallaxis and transfer.

Preferred application methods are into water bodies, via soil, cracks and crevices, pastures, manure piles, sewers, into water, on floor, wall, or by perimeter spray application and bait.

According to a preferred embodiment of the invention, the compounds of formula I are employed via soil application. Soil application is especially favorable for use against ants, termites, flies, crickets, or cockroaches.

According to another preferred embodiment of the invention, for use against non crop pests such as ants, termites, wasps, flies, mosquitoes, crickets, locusts, or cockroaches the compounds of formula I are prepared into a bait preparation.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickiness, moisture retention or aging characteristics.

The bait employed in the composition is a product which is sufficiently attractive to incite insects such as ants, termites, wasps, flies, mosquitoes, crickets etc. or cockroaches to eat it. This attractant may be chosen from feeding stimulants or para and/or sex pheromones. Suitable feeding stimulants are chosen, for example, from animal and/or plant proteins (meat-, fish- or blood meal, insect parts, crickets powder, egg yolk), from fats and oils of animal and/or plant origin, or mono-, oligo- or polyorgano-saccharides, especially from sucrose, lactose, fructose, dextrose, glucose, starch, pectin or even molasses or honey, or from salts such as ammonium sulfate, ammonium carbonate or ammonium acetate. Fresh or decaying parts of fruits, crops, plants, animals, insects or specific parts thereof can also serve as a feeding stimulant. Pheromones are known to be more insect specific. Specific pheromones are described in the literature and are known to those skilled in the art.

Formulations of compounds of formula I as aerosols (e.g in spray cans), oil sprays or pump sprays are highly suitable for the non-professional user for controlling pests such as flies, fleas, ticks, mosquitoes, locusts or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylfomaamide, N-methylpyrrolidone, dimethyl sulphoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

The compounds of formula I and its respective compositions can also be used in mosquito coils and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula I and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder.

The impregnation of curtains and bednets is mostly done by dipping the textile material into emulsions or dispersions of the insecticide or spraying them onto the nets.

The compounds of formula I are also suitable for the protection of the seed and the seedlings' roots and shoots, preferably the seeds, against soil pests.

Especially preferred is the protection of seeds from the group of cereals (e.g. wheat, barley, rye), canola, sugar beet, maize, sorghum, sunflower, cotton, rice, peas, colza, potato, and market-garden crops like rice, wheat, barley, or rye.

Conventional seed treatment formulations include for example flowable concentrates FS, solutions LS, powders for dry treatment DS, water dispersible powders WS or granules for slurry treatment, water soluble powders SS and emulsion ES. Application to the seeds is carried out before sowing, either directly on the seeds or after having pregerminated the latter.

Preferred are FS formulations.

Preferred FS formulations of compounds of formula I for seed treatment comprise from 0.5 to 80% of the active ingredient, from 0.05 to 5% of a wetter, from 0.5 to 15% of a dispersing agent, from 0.1 to 5% of a thickener, from 5 to 20% of an anti-freeze agent, from 0.1 to 2% of an anti-foam agent, from 1 to 20% of a pigment and/or a dye, from 0 to 15% of a sticker/adhesion agent, from 0 to 75% of a filler/vehicle, and from 0.01 to 1% of a preservative.

In the treatment of seed, the application rates of the compound of formula I or compositions comprising it are generally from 0.1 g to 10 kg per 100 kg of seed, preferably from 1 g to 5 kg per 100 kg of seed, in particular from 1 g to 2.5 kg per 100 kg of seed. For specific crops such as lettuce the rate can be higher.

In the control of pests, the application of the compound of formula I or of the composition comprising it is carried out by spraying or dusting the seeds, the plants or the soil (and thereby the seeds) before or after sowing of the plants or before or after emergence of the plants.

A further subject of the invention is a method of treating the seed in the seed drill with a granular formulation containing the active ingredient or a composition comprising it, with optionally one or more solid or liquid, agriculturally acceptable carriers and/or optionally with one or more agriculturally acceptable surfactants. This method is advantageously employed in seedbeds of cereal, maize, cotton and sunflower. For cereals and maize, the rates for compounds of formula I are between 50 and 500 g/ha.

The invention also relates to the propagation product of plants, and especially the treated seed comprising, that is, coated with and/or containing, a compound of formula I or a composition comprising it. The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

The seed comprises the inventive compounds or compositions comprising them in an amount of from 0.1 g to 10 kg per 100 kg of seed.

Compositions of this invention may also contain other active ingredients, for example other pesticides, insecticides, herbicides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

The following list of pesticides together with which the compounds according to the invention can be used, is intended to illustrate the possible combinations, but not to impose any limitation:

A.1. Organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

A.2. Carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

A.3. Pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

A.4. Growth regulators: a) chitin synthesis inhibitors: benzoylureas: chlorfluazuron, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

A.5. Nicotinic receptor agonists/antagonists compounds: clothianidin, dinotefuran, imidacloprid, thiamethoxam, nitenpyram, acetamiprid, thiacloprid; the thiazol compound of formula I'¹

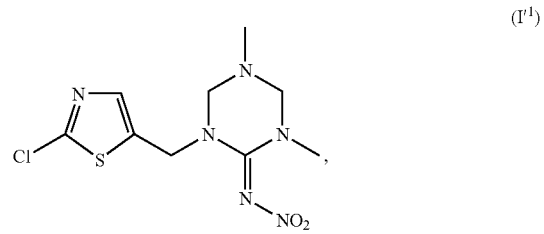

A.6. GABA antagonist compounds: acetoprole, endosulfan, ethiprole, fipronil, vaniliprole, pyrafluprole, pyriprole, the phenylpyrazole compound of formula I'²

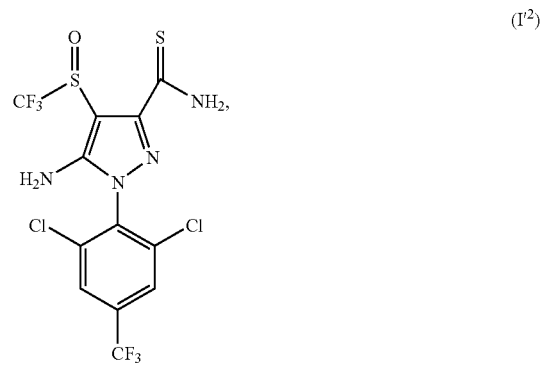

A.7. Macrocyclic lactone insecticides: abamectin, emamectin, milbemectin, lepimectin, spinosad, A.8. METI I compounds: fenazaquin, pyridaben, tebufenpyrad, tolfenpyrad, flufenerim;

A.9. METI II and III compounds: acequinocyl, fluacyprim, hydramethyinon;

A.10. Uncoupler compounds: chlorfenapyr;

A.11. Oxidative phosphorylation inhibitor compounds: cyhexatin, diafenthiuron, fenbutatin oxide, propargite;

A.12. Moulting disruptor compounds: cyromazine;

A.13. Mixed Function Oxidase inhibitor compounds: piperonyl butoxide;

A.14. Sodium channel blocker compounds: indoxacarb, metaflumizone,

A.15. Various: benclothiaz, bifenazate, cartap, flonicamid, pyridalyl, pymetrozine, sulfur, thiocyclam, flubendiamide, cyenopyrafen, flupyrazofos, cyflumetofen, amidoflumet, the aminoisothiazole compounds of formula I'³,

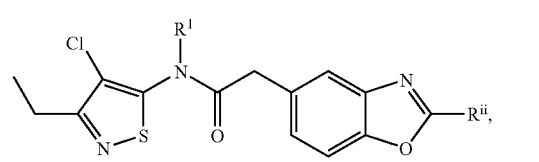

wherein $R^i$ is —$CH_2OCH_2CH_3$ or H and $R^{ii}$ is $CF_2CF_2CF_3$ or $CH_2CH(CH_3)_3$, the anthranilamide compounds of formula I'⁴

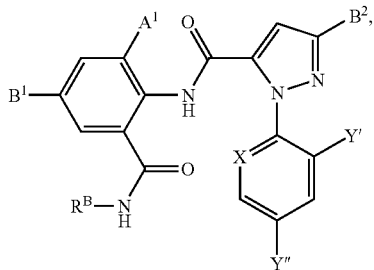

(I'⁴)

wherein $A^1$ is $CH_3$, Cl, Br, I, X is C—H, C—Cl, C—F or N, Y' is F, Cl, or Br, Y" is hydrogen, F, Cl, $CF_3$, $B^1$ is hydrogen, Cl, Br, I, CN, $B^2$ is Cl, Br, $CF_3$, $OCH_2CF_3$, $OCF_2H$, and $R^B$ is hydrogen, $CH_3$ or $CH(CH_3)_2$, and the malononitrile compounds as described in JP 2002 284608, WO 02/89579, WO 02/90320, WO 02/90321, WO 04/06677, WO 04/20399, JP 2004 99597, WO 05/68423, WO 05/68432, or WO 05/63694, especially the malononitrile compounds $CF_2HCF_2CF_2CF_2CH_2C(CN)_2CH_2CH_2CF_3$ (2-(2,2,3,3,4,4,5,5-octafluoropentyl)-2-(3,3,3-trifluoropropyl)malononitrile), $CF_3(CH_2)_2C(CN)_2CH_2(CF_2)_5CF_2H$ (2-(2,2,3,3,4,4,5,5,6,6,7,7-Dodecafluoro-heptyl)-2-(3,3,3-trifluoro-propyl)-malononitrile), $CF_3(CH_2)_2C(CN)_2(CH_2)_2C(CF_3)_2F$ (2-(3,4,4,4-Tetrafluoro-3-trifluoromethyl-butyl)-2-(3,3,3-trifluoro-propyl)-malononitrile), $CF_3(CH_2)_2C(CN)_2(CH_2)_2(CF_2)_3CF_3$ (2-(3,3,4,4,5,5,6,6,6-Nonafluoro-hexyl)-2-(3,3,3-trifluoro-propyl)-malononitrile), $CF_2H(CF_2)_3CH_2C(CN)_2 CH_2 (CF_2)_3CF_2H$ (2,2-Bis-(2,2,3,3,4,4,5,5-octafluoro-pentyl)-malononitrile), $CF_3(CH_2)_2C(CN)_2CH_2(CF_2)_3CF_3$ (2-(2,2,3,3,4,4,5,5,5-Nonafluoro-pentyl)-2-(3,3,3-trifluoro-propyl)-malononitrile), $CF_3(CF_2)_2CH_2C(CN)_2CH_2(CF_2)_3 CF_2H$ (2-(2,2,3,3,4,4,4-Heptafluoro-butyl)-2-(2,2,3,3,4,4,5,5-octafluoro-pentyl)-malononitrile) and $CF_3CF_2CH_2C(CN)_2 CH_2(CF_2)_3CF_2H$ (2-(2,2,3,3,4,4,5,5-Octafluoro-pentyl)-2-(2,2,3,3,3-pentafluoro-propyl)-malononitrile).

The commercially available compounds of the group A may be found in The Pesticide Manual, 13th Edition, British Crop Protection Council (2003) among other publications. Thiamides of formula I'² and their preparation have been described in WO 98/28279. Aminoisothiazole compounds of formula I'³ and their preparation have been described in WO 00/06566. Lepimectin is known from Agro Project, PJB Publications Ltd, November 2004. Benclothiaz and its preparation have been described in EP-A1 454621. Methidathion and Paraoxon and their preparation have been described in Farm Chemicals Handbook, Volume 88, Meister Publishing Company, 2001. Acetoprole and its preparation have been described in WO 98/28277. Metaflumizone and its preparation have been described in EP-A1 462 456. Flupyrazofos has been described in Pesticide Science 54, 1988, p.237-243 and in U.S. Pat. No. 4,822,779. Pyrafluprole and its preparation have been described in JP 2002193709 and in WO 01/00614. Pyriprole and its preparation have been described in WO 98/45274 and in U.S. Pat. No. 6,335,357. Amidoflumet and its preparation have been described in U.S. Pat. No. 6,221,890 and in JP 21010907. Flufenerim and its preparation have been described in WO 03/007717 and in WO 03/007718. Cyflumetofen and its preparation have been described in WO 04/080180. Anthranilamides of formula I'⁴ and their preparation have been described in WO 01/70671; WO 02/48137; WO 03/24222, WO 03/15518, WO 04/67528; WO 04/33468; and WO 05/118552. The malononitrile compounds $CF_2HCF_2CF_2CF_2CH_2C(CN)_2CH_2CH_2CF_3$ (2-(2,2,3,3,4,4,5,5-octafluoropentyl)-2-(3,3,3-trifluoropropyl)malononitrile), $CF_3(CH_2)_2C(CN)_2CH_2(CF_2)_5CF_2H$ (2-(2,2,3,3,4,4,5,5,6,6,7,7-Dodecafluoro-heptyl)-2-(3,3,3-trifluoro-propyl)-malononitrile), $CF_3(CH_2)_2C(CN)_2(CH_2)_2C(CF_3)_2F$ (2-(3,4,4,4-Tetrafluoro-3-trifluoromethyl-butyl)-2-(3,3,3-trifluoro-propyl)-malononitrile), $CF_3(CH_2)_2C(CN)_2(CH_2)_2 (CF_2)_3CF_3$ (2-(3,3,4,4,5,5,6,6,6-Nonafluoro-hexyl)-2-(3,3,3-trifluoro-propyl)-malononitrile), $CF_2H(CF_2)_3CH_2C(CN)_2 CH_2(CF_2)_3CF_2H$ (2,2-Bis-(2,2,3,3,4,4,5,5-octafluoro-pentyl)-malononitrile), $CF_3(CH_2)_2C(CN)_2CH_2(CF_2)_3CF_3$ (2-(2,2,3,3,4,4,5,5,5-Nonafluoro-pentyl)-2-(3,3,3-trifluoro-propyl)-malononitrile), $CF_3(CF_2)_2CH_2C(CN)_2CH_2(CF_2)_3 CF_2H$ (2-(2,2,3,3,4,4,4-Heptafluoro-butyl)-2-(2,2,3,3,4,4,5,5-octafluoro-pentyl)-malononitrile) and $CF_3CF_2CH_2C(CN)_2 CH_2(CF_2)_3CF_2H$ (2-(2,2,3,3,4,4,5,5-Octafluoro-pentyl)-2-(2,2,3,3,3-pentafluoro-propyl)-malononitrile) have been described in WO 05/63694.

Preferred are mixtures with N-R'-2,2-dihalo-1-R"cyclopropanecarboxamide-2-(2,6-dichloro-α,α,α-tri-fluoro-p-tolyl)hydrazone or N-R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl.

Some of the mixtures of the compounds of formula I with the above-mentioned pesticides are synergistic, that is, they contain the active mixing partner in synergistically effective amounts. Synergistic mixtures of compounds of formula I with the following pesticides are preferred:

Moreover, especially preferred with regard to their use according to the present invention are mixtures wherein the compound of formula II is selected from the groups A.3. (pyrethroids), A.4. (growth regulators), A.5. (nicotinic receptor agonists/antagonists compounds), A.6. (GABA antagonist compounds), A.7. (macrocyclic lactone insecticides), A.10.(uncoupler compounds), A.14. (sodium channel blocker compounds), or A.15. (various pesticide compounds).

Most preferred are mixtures wherein the compound of formula II is selected from the group A-1 consisting of bifenthrin, cyhalothrin, cypermethrin, alpha-cypermethrin, deltamethrin, lamda-cyhalothrin, permethrin; flufenoxuron, hexaflumuron, teflubenzuron, novaluron; clothianidin, acetamiprid, imidacloprid, thiamethoxam; fipronil, ethiprole; abmamectin, emamectin, spinosad; chlorfenapyr; indoxacarb, metaflumizone; anthranilamide compounds of formula I'⁴, malononitrile compounds as described in JP 2002 284608, WO 02/89579, WO 02/90320, WO 02/90321, WO 04/06677, WO 04/20399, JP 2004 99597, WO 05/68423, WO 05/68432, or WO 05/63694, especially the malononitrile compounds $CF_2HCF_2CF_2CF_2CH_2C(CN)_2CH_2CH_2CF_3$ (2-(2,2,3,3,4,4,5,5-octafluoropentyl)-2-(3,3,3-trifluoropropyl) malononitrile), $CF_3(CH_2)_2C(CN)_2CH_2(CF_2)_5CF_2H$ (2-(2,2,3,3,4,4,5,5,6,6,7,7-Dodecafluoro-heptyl)-2-(3,3,3-trifluoro-propyl)-malononitrile), $CF_3(CH_2)_2C(CN)_2(CH_2)_2C(CF_3)_2F$ (2-(3,4,4,4-Tetrafluoro-3-trifluoromethyl-butyl)-2-(3,3,3-trifluoro-propyl)-malononitrile), $CF_3(CH_2)_2C(CN)_2(CH_2)_2 (CF_2)_3CF_3$ (2-(3,3,4,4,5,5,6,6,6-Nonafluoro-hexyl)-2-(3,3,3-trifluoro-propyl)-malononitrile), $CF_2H(CF_2)_3CH_2C(CN)_2 CH_2(CF_2)_3CF_2H$ (2,2-Bis-(2,2,3,3,4,4,5,5-octafluoro-pentyl)-malononitrile), $CF_3(CH_2)_2C(CN)_2CH_2(CF_2)_3CF_3$ (2-(2,2,3,3,4,4,5,5,5-Nonafluoro-pentyl)-2-(3,3,3-trifluoro-propyl)-maiononitrile), $CF_3(CF_2)_2CH_2C(CN)_2CH_2(CF_2)_3 CF_2H$ (2-(2,2,3,3,4,4,4-Heptafluoro-butyl)-2-(2,2,3,3,4,4,5,5-octafluoro-pentyl)-malononitrile) and $CF_3CF_2CH_2C(CN)_2$ CH$_2$(CF$_2$)$_3$CF$_2$H (2-(2,2,3,3,4,4,5,5-Octafluoro-pentyl)-2-(2,2,3,3,3-pentafluoro-propyl)-malononitrile), pymetrazine, pyridalyl.

Synergistic mixtures of the compound of formula I: 1-(2,6-dichloro-4-trifluoromethylphenyl)-3-(1-methyl-2,2-dichlorocyclopropyl)-5-methyl-1,2,4-triazole with one of the pesticides of group A-1 below are especially preferred.

Also especially preferred are synergistic mixtures of the compound of formula I: 1-(2,6-dichloro-4-trifluoromethylphenyl)-3-(2,2-dichlorocyclopropyl)-5-methyl-1,2,4-triazole. with one of the pesticides of group A-1 below are especially preferred.

The synergistic mixtures advantageously reduce the dosage rate and/or enhance the spectrum of activity and/or combine know-down activity with prolonged control and/or resistance management. They allow enhanced control of pests compared to the control rates that are possible with the individual compounds.

The mixtures of compounds I and II, or the compounds I and II used simultaneously, that is jointly or separately, or in succession, the sequence, in the case of separate application, generally not having any effect on the result of the control measures, exhibit outstanding action against pests from the above-mentioned orders.

The compounds I and the compound II are usually applied in a weight ratio of from 100:1 to 1:100, preferably from 20:1 to 1:50, in particular from 5:1 to 1:20.

The synergistic mixtures according to the invention can be converted into the customary formulations as mentioned below for compounds of formula I. The ranges of the application rates also are as mentioned for compounds of formula I.

The insects may be controlled by contacting the target parasite/pest, its food supply, habitat, breeding ground or its locus with a pesticidally effective amount of compounds of or compositions of formula I.

"Locus" means a habitat, breeding ground, plant, seed, soil, area, material or environment in which a pest or parasite is growing or may grow.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

The compounds of formula I and its compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of formula I are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant control composition of the present invention is directly applied to the nest of the ants or to its surrounding or via bait contact.

The compounds or compositions of the invention can also be applied preventively to places at which occurrence of the pests is expected.

The compounds of formula I may also be used to protect growing plants from attack or infestation by pests by contacting the plant with a pesticidally effective amount of compounds of formula I. As such, "contacting" includes both direct contact (applying the compounds/compositions directly on the pest and/or plant—typically to the foliage, stem or roots of the plant) and indirect contact (applying the compounds/compositions to the locus of the pest and/or plant).

In the case of soil treatment or of application to the pests dwelling place or nest, the quantity of active ingredient ranges from 0.0001 to 500 g per 100 m$^2$, preferably from 0.001 to 20 g per 100 m$^2$. Soil treatment of termites (Isoptera) is an especially preferred embodiment of the present invention.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in bait compositions, the typical content of active ingredient is from 0.0001 weight % to 15 weight %, desirably from 0.001 weight % to 5% weight % of active compound. The composition used may also comprise other additives such as a solvent of the active material, a flavoring agent, a preserving agent, a dye or a bitter agent. Its attractiveness may also be enhanced by a special color, shape or texture.

For use in spray compositions, the content of active ingredient is from 0.001 to 80 weights %, preferably from 0.01 to 50 weight % and most preferably from 0.01 to 15 weight %.

For use in treating crop plants, the rate of application of the active ingredients of this invention may be in the range of 0.1 g to 4000 g per hectare, desirably from 25 g to 600 g per hectare, more desirably from 50 g to 500 g per hectare.

Compounds of formula I and compositions comprising them can also be used for controlling and preventing infestations and infections animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of formula I and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formula I and compositions comprising them are suitable for systemic and/or non-systemic control of ecto- and/or endoparasites. They are active against all or some stages of development.

The compounds of formula I are especially useful for combating ectoparasites.

The compounds of formula I are especially useful for combating parasites of the following orders and species, respectively:

fleas (Siphonaptera), e.g. *Ctenocephalides fells, Ctenocephalides canis, Xenopsylla cheopis, Pulex irritans, Tunga penetrans,* and *Nosopsyllus fasciatus,* cockroaches (Blaftaria—Blattodea), e.g. *Blattella germanica, Blattella asahinae, Periplaneta americana, Periplaneta japonica, Periplaneta brunnea, Periplaneta fuligginosa, Periplaneta australasiae,* and *Blafta orientalis,* flies, mosquitoes (Diptera), e.g. *Aedes aegypti, Aedes albopicus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chiysomya bezziana, Chrysomya hominivorax, Chrysomya macellaria, Chrysops discalis, Chrysops silacea, Chrysops aflanticus, Cochliomyla hominivorax, Cordylobia anthropophaga, Culicoides furens, Culex pipiens, Culex nigripalpus, Culex quinquefasciatus, Culex tarsalls, Culiseta inornata, Culiseta melanura, Dermatobia hominis, Fannia canicuiads, Gasterophilus intestinalis, Glossina morsitans, Glossina palpalis, Glossina fuscipes, Glossina tachinoides, Haematobia irritans, Haplodiplosis equestrds, Hippelates* spp., *Hypoderma lineata, Leptoconops torrens, Lucilia caprina, Lucilia cuprina, Lucilia sericata, Lycoria pectoralis, Mansonia* spp., *Musca domestics, Muscina stabulans, Oestrus ovis, Phlebotomus argentipes, Psorophora columbiae, Psorophora discolor, Prosimulium mixturn, Sarcophaga haemorrhoidalls, Sarcophaga* sp., *Simullum vfttatum, Stomoxys calcitrans, Tabanus bovinus, Tabanus atratus, Tabanus lineola,* and *Tabanus similis,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.* ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma amerdcanum, Ambryomma macuiatum, Ornithodorus hermsi, Ornithodorus turicata* and parasitic mites (Mesostigmata), e.g. *Ornithonyssus bacoi* and *Dermanyssus gallnae, Actinedida* (Prostigmata) and *Acaridida* (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp, Bugs (Heteropterida): *Cimex lectularius, Cimex hemipterus, Reduvius senilis, Triatoma* spp., *Rhodnius* ssp., *Panstrongylus* ssp. and *Arilus crltatus,*

Anoplurida, e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus., Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus,* and *Dioctophyma renale,*

Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi,*

Camallanida, e.g. *Dracunculus medinensis* (guinea worm)

Spirurida, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi,* and *Habronema* spp., Thorny headed worms (Acanthocephala), e.g. *Acanthocephalus* spp., *Macracanthorhynchus hirudinaceus* and *Oncicola* spp, Planarians (Plathelminthes):

Flukes (Trematoda), e.g. *Faciola* spp., *Fascioloides magna, Paragonimus* spp., *Dicrocoellum* spp., *Fasciolopsis buski, Clonorchis sinensis, Schistosoma* spp., *Trichobllharzia* spp., *Alaria alata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The compounds of formula I and compositions containing them are particularly useful for the control of pests from the orders Diptera, Siphonaptera and Ixodida, especially for control of mosquitoes.

The use of the compounds of formula I and compositions containing them for combating flies is a further preferred embodiment of the present invention.

Furthermore, the use of the compounds of formula I and compositions containing them for combating fleas is especially preferred.

The use of the compounds of formula I and compositions containing them for combating ticks is a further preferred embodiment of the present invention.

The compounds of formula I also are especially useful for combating endoparasites (roundworms nematoda, thorny headed worms and planarians).

Administration can be carried out both prophylactically and therapeutically.

Administration of the active compounds is carried out directly or in the form of suitable preparations, orally, topically/dermally or parenterally.

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Suitable preparations are:

Solutions such as oral solutions, concentrates for oral administration after dilution, solutions for use on the skin or in body cavities, pouring-on formulations, gels;

Emulsions and suspensions for oral or dermal administration; semi-solid preparations;

Formulations in which the active compound is processed in an ointment base or in an oil-in-water or water-in-oil emulsion base;

Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methyl-pyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropylenglycol monomethylether, ketons such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointment-like consistency results. The thickeners employed are the thickeners given above.

Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents which are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethylacetamide, n-alkylpyrrolidones such as methylpyrrolidone, n-butylpyrrolidone or n-octylpyrrolidone, N-methylpyrrolidone, 2-pyrrolidone, 2,2-dimethyl-4-oxy-methylene-1,3-diox-olane and glycerol formal.

Suitable colorants are all colorants permitted for use on animals and which can be dissolved or suspended.

Suitable absorption-promoting substances are, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants are sulfites or metabisulfites such as potassium metabisulfite, ascorbic acid, butylhydroxytoluene, butylhydroxyanisole, tocopherol.

Suitable light stabilizers are, for example, novantisolic acid.

Suitable adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable hydrophobic phases (oils) are:

liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_8$-$C_{12}$ or other specially selected natural fatty acids, partial glyceride mixtures of saturated or unsaturated fatty acids possibly also containing hydroxyl groups, mono- and diglycerides of the $C_8$-$C_{10}$ fatty acids, fatty acid esters such as ethyl stearate, di-n-butyryl adipate, hexyl laurate, dipropylene glycol perlargonate, esters of a branched fatty acid of medium chain length with saturated fatty alcohols of chain length C16-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof.

Suitable hydrophilic phases are: water, alcohols such as propylene glycol, glycerol, sorbitol and mixtures thereof.

Suitable emulsifiers are:

non-ionic surfactants, e.g. polyethoxylated castor oil, polyethoxylated sorbitan monooleate, sorbitan monostearate, glycerol monostearate, polyoxyethyl stearate, alkylphenol polyglycol ether;

ampholytic surfactants such as di-sodium N-lauryl-p-iminodipropionate or lecithin;

anionic surfactants, such as sodium lauryl sulfate, fatty alcohol ether sulfates, mono/dialkyl polyglycol ether orthophosphoric acid ester monoethanolamine salt;

cation-active surfactants, such as cetyltrimethylammonium chloride.

Suitable further auxiliaries are: substances which enhance the viscosity and stabilize the emulsion, such as carboxymethylcellulose, methyicellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries which may be mentioned are those given above.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

The compositions which can be used in the invention can comprise generally from about 0.001 to 95% of the compound of formula I.

Generally it is favorable to apply the compounds of formula I in total amounts of 0.5 mg/kg to 100 mg/kg per day, preferably 1 mg/kg to 50 mg/kg per day.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 per cent by weight.

Furthermore, the preparations comprise the compounds of formula I against endoparasites in concentrations of 10 ppm to 2 percent by weight, preferably of 0.05 to 0.9 per cent by weight, very particularly preferably of 0.005 to 0.25 percent by weight.

In a preferred embodiment of the present invention, the compositions comprising the compounds of formula I them are applied dermally/topically.

In a further preferred embodiment, the topical application is conducted in the form of compound-containing shaped articles such as collars, medallions, ear tags, bands for fixing at body parts, and adhesive strips and foils.

Generally it is favorable to apply solid formulations which release compounds of formula I in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the compounds of formula I. A detailed list of plastics and elastomers as well as preparation procedures for the shaped articles is given e.g. in WO 03/086075.

The active compounds can also be used as a mixture with synergists or with other active compounds which act against pathogenic endo- and ectoparasites. The following list of pesticides together with which the compounds according to the invention can be used for controlling and preventing infestations and infections in warm-blooded animals and fish, is intended to illustrate the possible combinations, but not to impose any limitation:

Organophosphates: Acephate, Chlorfenvinphos, Diazinon, Dichlorvos, Dicrotophos, Dimethoate, Ethion, Fenitrothion, Fenthion, Isoxathion, Malathion, Phenthoate, Phosalone, Phosmet, Phoxim, Pirimiphos-methyl, Profenofos, Prothiofos, Sulprophos, Triazophos, Trichlorfon, Quintiofos, Coumaphos, Chlorphoxim, Bromophos-ethyl, 2,3-p-Dioxanedithiol-S,S-bis(O,O-diethylphosphorodithionat);

Carbamates: Alanycarb, Benfuracarb, Carbaryl, Carbosulfan, Fenoxycarb, Furathiocarb, Indoxacarb, Triazamate;

Pyrethroids: alpha-Cypermethrin, Deltamethrin, Ethofenprox, Fenvalerate, Cyhalothrin, Lambda-Cyhalothrin, Permethrin, Silafluofen, Tau-Fluvalinate, Tralomethrin, Zeta-Cypermethrin, Flumethrin, Cyfluthrin and its enantiomers and stereomers, Cypermethrin;

Arthropod growth regulators: a) chitin synthesis inhibitors: benzoylureas: Chlorfluazuron, Cyromazine, Diflubenzuron, Flucycloxuron, Flufenoxuron, Hexaflumuron, Lufenuron, Novaluron, Teflubenzuron, Triflumuron; Buprofezin, Diofenolan, Hexythiazox, Etoxazole, Clofentazine; b) ecdysone antagonists: Halofenozide, Methoxyfenozide, Tebufenozide; c) juvenoids: Pyriproxyfen, Methoprene, Fenoxycarb; d) lipid biosynthesis inhibitors: Spirodiclofen;

(Neo)nicotinoids: Acetamiprid, Clothianidin, Flonicamid, Imidacloprid, Nitenpyram, Thiacloprid, Thiamethoxam;

Synthetic coccidiosis compounds, polyetherantibiotics: Amprolium, Robenidin, Toltrazuril, Monensin, Salinomycin, Maduramicin, Lasalocid, Narasin, Semduramicin;

Various: Abamectin (Avermectins), Acequinocyl, Amitraz, Azadirachtin, Bifenazate, *Bacillus thuringiensis, Bacillus subtills,* Cartap, Chlorfenapyr, Chlordimeform, Cyromazine, Diafenthiuron, Dinetofuran, Diofenolan, Emamectin, Endosulfan, Epsiprantel, Ethiprole, Fenazaquin, Fipronil, Formetanate, Formetanate hydrochloride, Hydramethylnon, Indoxacarb, Metaflumizone, L-2,3,5,6-tetrahydro-6-phenyl-imidazothiazole, Levamisole, Milbemectin (Milbemycins), Moxidectin, Praziquantel, Pyrantel, Pyridaben, Pymetrozine, Selamectin, Spinosad, Sulfur, Tebufenpyrad, and Thiocyclam.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

SYNTHESIS EXAMPLES

The compounds I obtained according to the protocols shown in the synthesis examples below together with their physical data are listed in Table I which follows.

Example 1

Preparation of 3-(2,2-Dichloro-1-methyl-cyclopropyl)-1-(2,6-dichloro-4-trifluoromethyl-phenyl)-5-methyl-1H-[1,2,4]triazole 50 g N-[1-(2,2,-Dichloro-1-methyl-cyclopropyl)-ethylidene]-N'-(2,6-dichloro-4-trifluoro-methylphenyl)-hydrazine and 17.9 ml pyridine were dissolved in 1 L toluene. At 0-5° C., 51 g DDQ was added portionwise. After stirring at 25° C. for 12 hours, 1 L 5% NaOH solution was added, the mixture was extracted with ether and dried with MgSO₄. Removal of the solvent gave 48.6 g of the above compound (mp. 107-116° C.).

TABLE I

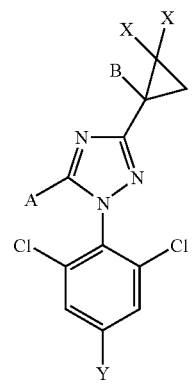

(I)

| No. | X | Y | A | B | Physical data (m.p.[° C.]/$^1$H-NMR(CDCl$_3$): d [ppm]) |
|---|---|---|---|---|---|
| I-1 | Cl | CF$_3$ | CH$_3$ | H | 8.21 (s), 7.77 (s), 2.58 (d), 1.87 (s), 1.66 (d). |
| I-2 | Cl | CF$_3$ | H | CH$_3$ | 133-138 |
| I-3 | Cl | CF$_3$ | CH$_3$ | CH$_3$ | 107-116 |
| Compound from EP 957 094 | | | | | |
| A | Cl | CF$_3$ | H | H | 8.20 (s), 7.76 (s), 3.10 (dd), 2.34 (t), 2.09 (dd). |

Examples of Action Against Pests

Test Methodology

Examples of Action Against Pests and Parasites

1. Activity against Argentine ant (*Linepithema humile*), harvester ant (*Pogonomyrmex californicus*), acrobat ant (*Crematogaster* spp.), carpenter ant (*Camponotus floridanus*), fire ant (*Solenopsis invicta*), house fly (*Musca domestica*), stable fly (*Stomoxys calcitrans*), flesh fly (*Sarcophaga* sp.), yellow-fever mosquito (*Aedes aegyptil*), house mosquito (*Culex quinquefasciatus*), malaria mosquito (*Anopheles albimanus*), German cockroach (*Blattella Germanica*), cat flea (*Ctenocephalides felis*), and brown dog tick (*Rhipicephalus sanguineus*) via glass contact Glass vials were treated with 0.5 ml of a solution of active ingredient in acetone and allowed to dry. Insects or ticks were placed into each vial together with some food and moisture supply. The vials were kept at 22° C. and were observed for treatment effects at various time intervals.

In these tests, compound I-3 at a rate of 0.1 ppm showed 100% mortality of *Aedes aegypti* at 24 hours after treatment.

Furthermore, compound I-3 at a rate of 5 ppm showed 100% mortality of *Musca domestilca* and *Blattella Germanica* at 24 hours after treatment.

Furthermore, compound I-3 at a rate of 10 ppm showed 100% mortality of *Crematogaster* spp. at 24 hours after treatment.

2. Activity against Argentine ant (*Linepithema humile*), acrobat ant (*Crematogaster* spp.), carpenter ant (*Camponotus floridanus*), fire ant (*Solenopsis invicta*), and eastern subterranean termite (*Reticulitermes flavipes*) via soil contact For ants, tests were conducted in Petri dishes. A thin layer of 1% agar in water was dispensed into the dishes and Florida sandy soil was spread over the agar. The active ingredient was dissolved in acetone and dispensed over the sand. Dishes were vented to evaporate the acetone, infested with ants, and covered. A 20% honey water solution was placed in each dish. The dishes were maintained at 22° C. and observed for mortality at various time intervals.

For termites, a thin layer of 1% agar was dispensed into Petri dishes. A thin layer of pre-treated soil was spread over the agar. For soil treatment, the active ingredient was diluted in acetone on a weight-to-weight basis and incorporated into the soil. Termite workers were introduced into each dish. Filter paper served as a food source. Test dishes were held at about 25° C. Termites were observed daily for mortality (dead or unable to stand upright and showing only weak movement).

In these tests, compound I-3 at a rate of 1 weight % showed 100% mortality of Reticulitermes flavipes at 3 days after treatment.

Furthermore, compound I-3 at a rate of 10 ppm showed 100% mortality of Camponotus floridanus at 24 hours after treatment.

3. Activity against Argentine ant (Linepithema humile), acrobat ant (Crematogaster spp.), carpenter ant (Camponotus floridanus), fire ant (Solenopsis invicta), house fly (Musca domestica), eastern subterranean termite (Reticulitermes flavipes), Formosan subterranean termite (Coptotermes formosanus), and German cockroach (Blattella Germanica) via bait For Argentine ant, acrobat ant, and carpenter ant, tests were conducted in Petri dishes. Baits were prepared with either honey/water solutions or ground cat chow. Active ingredient in acetone was added to the bait. 0.2 ml of treated honey water solution or 150 mg of treated cat chow, placed in a cap, was added to each dish. The dishes were covered and maintained at a temperature of 22° C. The ants were observed for mortality daily.

For the fire ants, corn grit was used as a bait matrix (0.1% active ingredient). Fire ant adults were placed into Petri dishes together with the bait. The ants were observed for mortality daily.

For house flies, bait tests were conducted with adults aged 2-5 days post-emergence. Active ingredient in acetone was applied to a bait matrix consisting of a mixture of powdered milk and sugar. House flies were placed into bait jars which were held at about 22° C. and were observed at 4 hours after treatment for knockdown (death plus morbidity (unable to stay upright)).

For termites, active ingredient in acetone was applied to filter papers. % a.i. were calculated on basis of the weight of the filter paper. Bioassays were conducted with one treated filter and ca. 30 termite workers per test Petri dish. Test dishes were maintained at 25° C. and observed daily for mortality (dead or moribund insects) or intoxication.

For cockroaches, boxes with ventilated lids were used as test arenas. The bait was prepared using ground cat chow, and the active ingredient in acetone was incorporated on a weight-to-weight ratio (0.03 grams of bait per box). The boxes were maintained at 22° C. and observed daily for mortality of the cockroaches.

In these tests, compound I-3 at a rate of 0.005 weight % showed 100% mortality of Reticulitermes flavipes at three days after treatment.

4. Activity against yellowfever mosquito (Aedes aegyptii), house mosquito (Culex quinquefasciatus) and malaria mosquito (Anopheles albimanus) larvae via water treatment Well plates were used as test arenas. The active ingredient was dissolved in acetone 30 and diluted with water to obtain the concentrations needed. The final solutions containing appr. 1% acetone were placed into each well. Approximately 10 mosquito larvae ($4^{th}$-instars) in 1 ml water were added to each well. Larvae were fed one drop of liver powder each day. The dishes were covered and maintained at 22° C. Mortality was recorded daily and dead larvae and live or dead pupae were removed daily. At the end of the test remaining live larvae were recorded and percent mortality was calculated.

5. Activity against cotton aphid (aphis gossypii)

The active compounds were formulated in 50:50 acetone: water and 100 ppm Kinetic™ surfactant.

Cotton plants at the cotyledon stage (one plant per pot) were infested by placing a heavily infested leaf from the main colony on top of each cotyledon. The aphids were allowed to transfer to the host plant overnight, and the leaf used to transfer the aphids was removed. The cotyledons were dipped in the test solution and allowed to dry. After 5 days, mortality counts were made.

In this test, compound I-3 at 300 ppm showed 100% mortality.

6. Activity against green peach aphid (Myzus persicae)

The active compounds were formulated in 50:50 acetone: water and 100 ppm Kinetic™ surfactant.

Pepper plants in the $2^{nd}$ leaf-pair stage (variety 'California Wonder') were infested with approximately 40 laboratory-reared aphids by placing infested leaf sections on top of the test plants. The leaf sections were removed after 24 hr. The leaves of the intact plants were dipped into gradient solutions of the test compound and allowed to dry. Test plants were maintained under fluorescent light (24 hour photoperiod) at about 25° C. and 20-40% relative humidity. Aphid mortality on the treated plants, relative to mortality on check plants, was determined after 5 days.

In this test, compound I-3 at 300 ppm showed 100% mortality, whereas compound A at 300 ppm show no effect.

7. Activity against bean aphid (aphis fabae)

The active compounds were formulated in 50:50 acetone: water and 100 ppm Kinetic™ surfactant.

Nasturtium plants grown in Metro mix in the $1^{st}$ leaf-pair stage (variety 'Mixed Jewle') were infested with approximately 2-30 laboratory-reared aphids by placing infested cut plants on top of the test plants. The cut plants were removed after 24 hr. Each plant was dipped into the test solution to provide complete coverage of the foliage, stem, protruding seed surface and surrounding cube surface and allowed to dry in the fume hood. The treated plants were kept at about 25° C. with continuous fluorescent light. Aphid mortality was determined after 3 days.

In this test, compounds I-1 and I-3 at 300 ppm showed 100% mortality, whereas compound A showed no effect.

8. Activity against silverleaf whitefly (bemisia argentifolii)

The active compounds were formulated in 50:50 acetone: water and 100 ppm Kinetic™ surfactant.

Selected cotton plants were grown to the cotyledon state (one plant per pot). The cotyledons were dipped into the test solution to provide complete coverage of the foliage and placed in a well-vented area to dry. Each pot with treated seedling was placed in a plastic cup and 10 to 12 whitefly adults (approximately 3-5 day old) were introduced. The insects were colleted using an aspirator and an 0.6 cm, non-toxic Tygon® tubing (R-3603) connected to a barrier pipette tip. The tip, containing the collected insects, was then gently inserted into the soil containing the treated plant, allowing insects to crawl out of the tip to reach the foliage for feeding. The cups were covered with a reusable screened lid (150 micron mesh polyester screen PeCap from Tetko Inc). Test plants were maintained in the holding room at about 25° C. and 20-40% relative humidity for 3 days avoiding direct exposure to the fluorescent light (24 hour photoperiod) to prevent trapping of heat inside the cup. Mortality was assessed 3 days after treatment of the plants.

In this test, compounds I-1 and I-3 at 300 ppm showed 100% mortality.

9. Activity against brown planthopper (*nilaparvata lugens*)

The active compounds were formulated in 50:50 acetone:water. Potted rice seedlings were sprayed with 10 ml test solution, air dried, placed in cages and inoculated with 10 adults. Percent mortality was recorded after 24, 72 and 120 hours.

In this test, compounds I-1, I-2 and I-3 at 300 ppm showed 100% mortality.

10. Activity against cowpea aphid (*aphis craccivora*)

The active compounds were formulated in 50:50 acetone:water. Potted cowpea plants colonized with 100-150 aphids of various stages were sprayed after the pest population has been recorded. Population reduction was recorded after 24, 72, and 120 hours.

In this test, compounds I-1, I-2 and I-3 at 300 ppm showed 100% mortality, whereas compound A showed no effect.

11. Activity against diamond back moth (*plutella xylostella*)

The active compounds were formulated in 50:50 acetone:water and 0.1% (vol/vol) Alkamuls EL 620 surfactant. A 6 cm leaf disk of cabbage leaves was dipped in the test solution for 3 seconds and allowed to air dry in a Petri plate lined with moist filter paper. The leaf disk was inoculated with 10 third instar larvae and kept at 25-27° C. and 50-60% humidity for 3 days. Mortality was assessed after 72 h of treatment. In this test, compounds I-1 and I-3 at 300 ppm showed 100% mortality, whereas compound A showed no effect.

12. Pesticidal action of synergistic mixtures of compounds of formula I

Potato plants for Colorado potato beetle and two-leaf cotton plants for tobacco budworm were utilized for bioassays. Excised plant leaves were dipped into 1:1 acetone/water dilutions of the active compounds. After the leaves had dried, they were individually placed onto water-moistened filter paper on the bottoms of Petri dishes. Each dish was infested with 5-7 larvae and covered with a lid. Each treatment dilution was replicated 4 times. Test dishes were held at approximately 27° C. and 60% humidity. Numbers of live and morbid larvae were assessed in each dish at 5 days after treatment application, and percent mortality was calculated.

To determine if an insecticidal mixture was synergistic, Limpel's formula was used:

$$E=X+Y-XY/100$$

E=Expected % mortality of the mixture
X=% mortality of compound X, as measured independently
Y=% mortality of compound Y, as measured independently Synergism was evident if the % observed mortality for the mixture was greater than the % expected mortality.

TABLE 1

Activity of mixtures of compound I-3 with alpha-cypermethrin

| Active | Dose rate [ppm] | % Mortality of Colorado Potato Beetle | % Mortality of Tobacco Budworm |
|---|---|---|---|
| I-3 | 300 | | 71.4 |
|  | 100 | 12.5 | 0 |
| alpha-cypermethrin | 0.06 | 17.5 | 7.2 |
|  | 0.03 | | 0 |

| I-3 + alpha-cypermethrin | | % mortality observed | % mortality expected | % mortality observed | % mortality expected |
|---|---|---|---|---|---|
| | 300 + 0.06 | | | 92.9 | 73.5 |
| | 300 + 0.03 | | | 82.1 | 71.4 |
| | 100 + 0.06 | 79.2 | 27.8 | 82.1 | 7.2 |
| | 100 + 0.03 | | | 17.9 | 0 |

The invention claimed is:

1. A compound of formula (I)

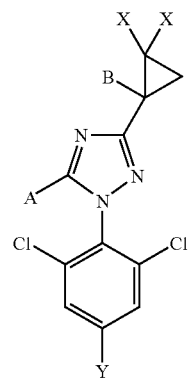

wherein
X is chloro or bromo;
Y is chloro or trifluormethyl; and
A and B are hydrogen or methyl with the proviso that one of A or B must be methyl;
or the enantiomers or salts thereof.

2. The compound of claim 1, wherein B is methyl and X is chloro.

3. The compound of claim 1, wherein A is methyl and X is chloro.

4. A compound: 1-(2,6-dichloro-4-trifluoromethylphenyl)-3-(1-methyl-2,2-dichlorocyclopropyl)-5-methyl-1,2,4-triazole.

5. A method for the control of insects or acarids comprising:
contacting the insect or acarid or their food supply, habitat or breeding grounds with a pesticidally effective amount of a composition or a compound of formula I:

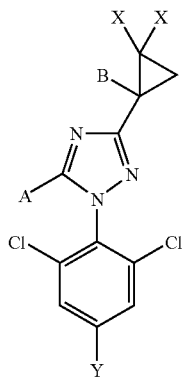

wherein
    X is chloro or bromo;
    Y is chloro or trifluormethyl; and
    A and B are hydrogen or methyl with the proviso that one of A or B must be methyl;
or the enantiomers or salts thereof;
wherein said insects or said acarids are controlled.

6. The method of claim 5, wherein the insects or acarids are selected from the Isoptera, Diptera, Blattaria (Blattodea), Hymenoptera, Siphonaptera and Acarina orders.

7. A method of protecting growing plants from attack or infestation by insects or acarids comprising:
    applying to the foliage of the plants, or to the soil or water in which they are growing, a pesticidally effective amount of a composition or a compound of formula I:

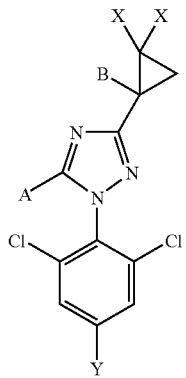

wherein
    X is chloro or bromo;
    Y is chloro or trifluormethyl; and
    A and B are hydrogen or methyl with the proviso that one of A or B must be methyl;
or the enantiomers or salts thereof;
wherein said growing plants are protected from attack or infestation by insects or acarids.

8. The method of claim 7, wherein the insects or acarids are selected from the Isoptera, Diptera, Blattaria (Blattodea), Hymenoptera, Siphonaptera and Acarina orders.

9. A method for treating, controlling, or protecting animals against infestation or infection by parasites comprising: orally, topically or parenterally administering or applying to animals a parasiticidally effective amount of compositions or compounds of formula I:

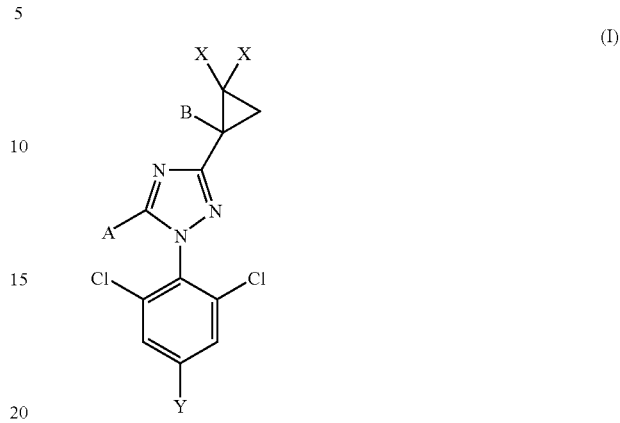

wherein
    X is chloro or bromo;
    Y is chloro or trifluormethyl; and
    A and B are hydrogen or methyl with the proviso that one of A or B must be methyl;
or the enantiomers or veterinarily acceptable salts thereof;
wherein said animals are controlled, or protected from infestation or infection by said parasites.

10. A process for the preparation of a composition for treating, controlling, or protecting animals against infestation or infection by parasites comprising:
    combining a parasiticidally effective amount of compositions or compounds of formula I:

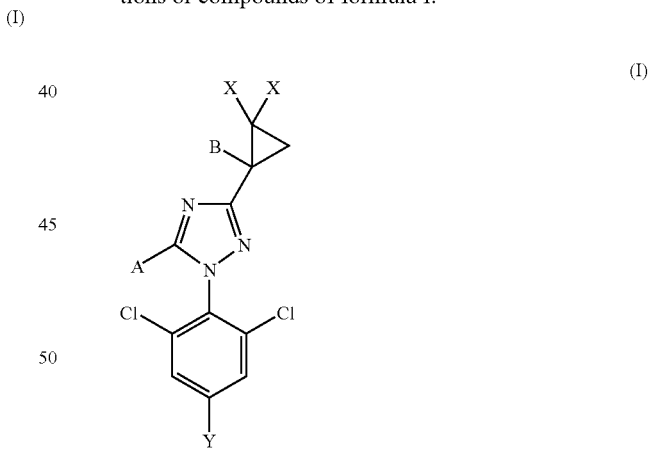

wherein
    X is chloro or bromo;
    Y is chloro or trifluormethyl; and
    A and B are hydrogen or methyl with the proviso that one of A or B must be methyl;
or the enantiomers or veterinarily acceptable salts thereof; and
a veterinarily acceptable carrier.

11. The process as claimed in claim 10 wherein the parasites are selected from the Diptera, Siphonaptera, and Ixodida orders.

12. A composition comprising:

a pesticidally or parasiticidally active amount of compounds of formula I

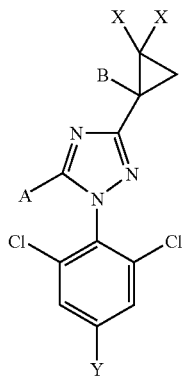

wherein
  X is chloro or bromo;
  Y is chloro or trifluormethyl; and
  A and B are hydrogen or methyl with the proviso that one of A or B must be methyl;
or the enantiomers or veterinarily acceptable salts thereof; and an agronomically or veterinarily acceptable carrier.

13. A synergistic mixture comprising:
a compound of formula I

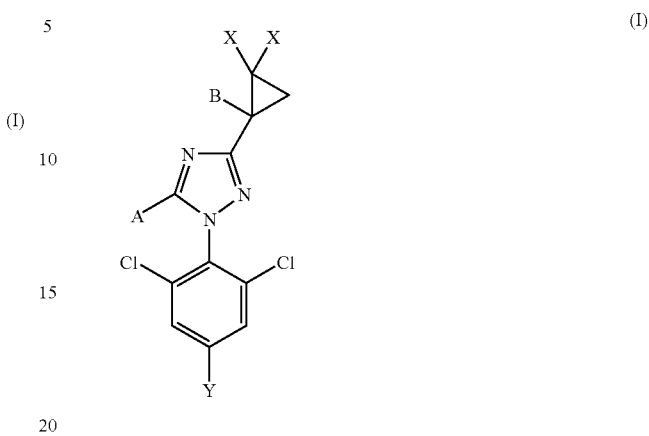

wherein
  X is chloro or bromo;
  Y is chloro or trifluormethyl; and
  A and B are hydrogen or methyl with the proviso that one of A or B must be methyl;
or the enantiomers or salts thereof;
and at least one other pesticide in synergistically effective amounts,
  wherein the observed mortality of the synergistic mixture of the compound of formula I and the at least one other pesticide is greater than the expected mortality of the compound of formula I and the at least one other pesticide.

* * * * *